US00PP28459P2

(12) United States Plant Patent
Nguyen

(10) Patent No.: US PP28,459 P2
(45) Date of Patent: Sep. 26, 2017

(54) ***ANGELONIA* PLANT NAMED 'BALARCHER'**

(50) Latin Name: *Angelonia angustifolia*
Varietal Denomination: Balarcher

(71) Applicant: Ball Horticultural Company, West Chicago, IL (US)

(72) Inventor: Phuong N. Nguyen, Thousand Oaks, CA (US)

(73) Assignee: Ball Horticultural Company, West Chicago, IL (US)

( * ) Notice: Subject to any disclaimer, the term of this patent is extended or adjusted under 35 U.S.C. 154(b) by 71 days.

(21) Appl. No.: 14/998,881

(22) Filed: Feb. 25, 2016

(51) Int. Cl.
*A01H 5/02* (2006.01)

(52) U.S. Cl.
USPC ..... Plt./404

(58) Field of Classification Search
USPC ..... Plt./263.1, 404
See application file for complete search history.

*Primary Examiner* — Susan McCormick Ewoldt
*Assistant Examiner* — Karen Redden
(74) *Attorney, Agent, or Firm* — Audrey Charles

(57) ABSTRACT

A new and distinct cultivar of *Angelonia* plant named 'Balarcher', characterized by its medium cherry-red colored flowers, dark green-colored foliage, and moderately vigorous, upright growth habit, is disclosed.

1 Drawing Sheet

Latin name of genus and species of plant claimed: *Angelonia angustifolia.*
Variety denomination: 'Balarcher'.

BACKGROUND OF THE INVENTION

The present invention relates to a new and distinct cultivar of *Angelonia* plant botanically known as *Angelonia angustifolia* and hereinafter referred to by the cultivar name 'Balarcher'.

The new cultivar originated in a controlled breeding program in Arroyo Grande, Calif. during September 2012. The objective of the breeding program was the development of *Angelonia* cultivars having large flowers, unique flower coloration, continuous flowering, and a vigorous, freely branching, and upright to semi-upright growth habit.

The new *Angelonia* cultivar is the result of cross-pollination. The female (seed) parent of the new cultivar is the proprietary *Angelonia angustifolia* breeding selection coded PN5828-5, not patented, characterized by its salmon and hot-pink colored flowers, dark green-colored foliage, and moderately vigorous, upright growth habit. The male (pollen) parent of the new cultivar is the proprietary *Angelonia angustifolia* breeding selection coded PN5719-6, not patented, characterized by its salmon and hot-pink colored flowers, dark green-colored foliage, and moderately vigorous, upright growth habit. The new cultivar was discovered and selected as a single flowering plant within the progeny of the above stated cross-pollination during July 2013 in a controlled environment in Arroyo Grande, Calif.

Asexual reproduction of the new cultivar by terminal stem cuttings since July 2013 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balarcher' as a new and distinct cultivar of *Angelonia* plant:

1. Medium cherry-red colored flowers;
2. Dark green-colored foliage; and
3. Moderately vigorous, upright growth habit.

Plants of the new cultivar differ from plants of the female and male parents primarily in flower color.

Of the many commercially available *Angelonia* cultivars, the most similar in comparison to the new cultivar is Archangel Dark Rose 'Balarcrose', U.S. Plant Pat. No. 25,992. However, in side by side comparisons, plants of the new cultivar differ from plants of 'Balarcrose' in at least the following characteristics:

1. Plants of the new cultivar have larger flowers than plants of 'Balarcrose'; and
2. Plants of the new cultivar have a flower petal color different from plants of 'Balarcrose'. Flower petals of the new cultivar have more red coloration than flower petals of 'Balarcrose'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balarcher'. The plants were grown in 4.5-inch pots for 8 weeks in a greenhouse in West Chicago, Ill. Plants were given one pinch at transplant.

DETAILED BOTANICAL DESCRIPTION

Figure 1:
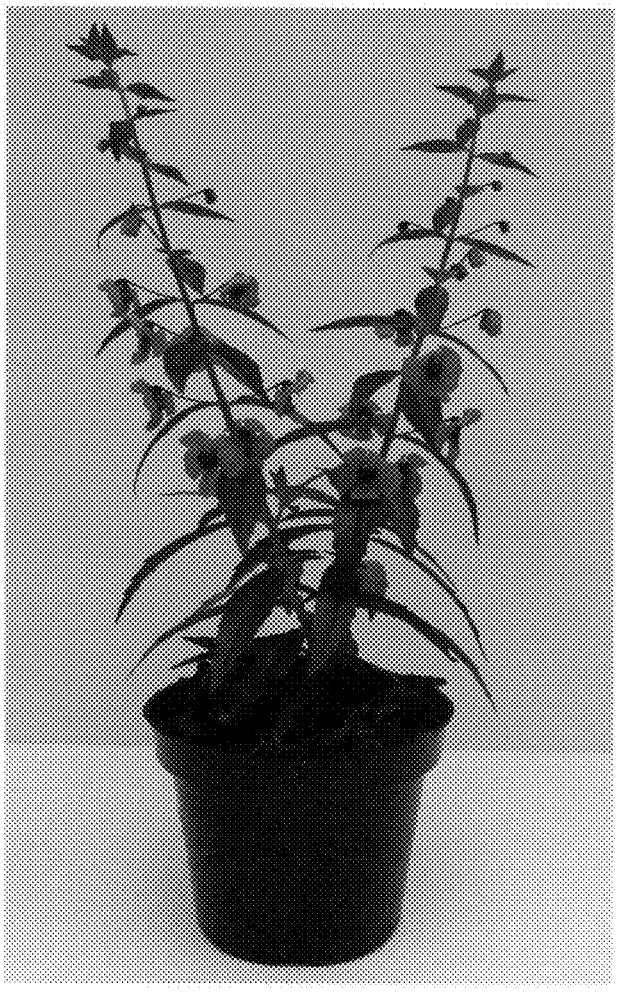
FIG. 1 illustrates a side view of the overall growth and flowering habit of 'Balarcher'.
Figure 2:
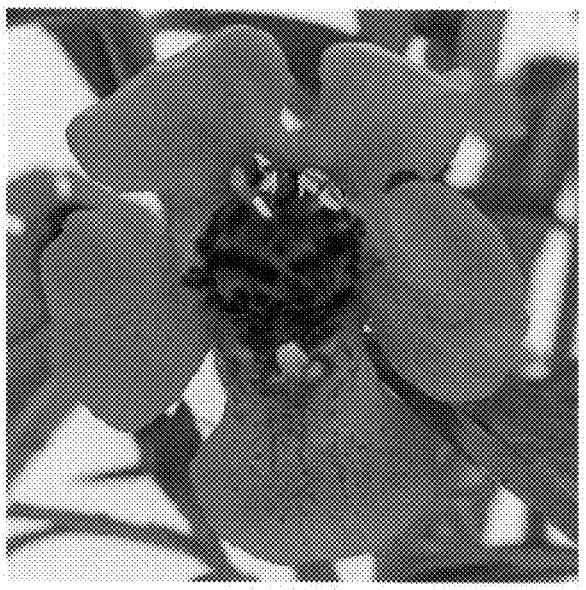
FIG. 2 illustrates a close-up view of an individual inflorescence of 'Balarcher'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in November 2015 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 8 weeks utilizing a soilless growth medium. Plants were given one pinch at transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Angelonia angustifolia* cultivar Balarcher.

Parentage:

*Female parent.*—Proprietary *Angelonia angustifolia* breeding selection coded PN5828-5, not patented.

*Male parent.*—Proprietary *Angelonia angustifolia* breeding selection coded PN5719-6, not patented.

Propagation:

*Type cutting.*—Terminal stem.

*Time to initiate roots.*—Approximately 7 to 9 days.

*Time to produce a rooted cutting.*—Approximately 24 to 28 days.

*Root description.*—Fine, fibrous.

*Rooting habit.*—Freely branching.

Plant description:

*Commercial crop time.*—Approximately 5 to 8 weeks from a rooted cutting to finish in a 10 cm pot.

*Growth habit and general appearance.*—Moderately vigorous, upright.

*Size.*—Height from soil level to top of plant plane: Approximately 30.5 cm. Width: Approximately 20.0 cm.

*Branching habit.*—Freely branching. Quantity of main branches per plant: Approximately 2.

*Branch.*—Shape: Square in cross section. Strength: Moderate, somewhat brittle. Length: Approximately 30.0 cm. Diameter: Approximately 3.0 mm. Length of central internode: Approximately 2.1 cm. Texture: Glabrous. Color of young and mature stems: 144B.

Foliage description:

*General description.*—Quantity of leaves per main branch: Approximately 28. Fragrance: None. Form: Simple. Arrangement: Opposite.

*Leaves.*—Aspect: Perpendicular or obtuse angle to stem. Shape: Elliptic. Margin: Widely serrate. Apex: Acute. Base: Sessile. Venation pattern: Pinnate. Length of mature leaf: Approximately 8.0 cm. Width of mature leaf: Approximately 1.7 cm. Texture of upper and lower surfaces: Sparsely glandular pubescent. Color of upper surface of young foliage: 137A with indistinguishable venation. Color of lower surface of young foliage: 137C with midvein of 146D, other venation indistinguishable. Color of upper surface of mature foliage: Closest to, but darker than N137A with indistinguishable venation. Color of lower surface of mature foliage: Closest to 137B with midvein of 146D, other venation indistinguishable.

Flowering description:

*Flowering habit.*—'Balarcher' is freely flowering under outdoor growing conditions with substantially continuous blooming from spring through autumn and year-round in greenhouse environment.

*Lastingness of individual flower on the plant.*—Approximately 7 to 10 days.

Inflorescence description:

*General description.*—Type: Terminal raceme. Quantity per plant: Approximately 2. Fragrance: Slight, sweet. Length or height: Approximately 21.5 cm. Width: Approximately 7.5 cm. Quantity of fully open flowers per inflorescence: Approximately 10.

Flower description:

*Type.*—Solitary, zygomorphic.

*Bud.*—Rate of opening: Generally takes 3 to 4 days for bud to progress from first color to fully open flower.

*Bud just before opening.*—Shape: Globular. Length: Approximately 6.0 mm. Diameter: Approximately 6.0 mm. Color of upper surface: 145A. Color of lower surface: 146B.

*Corolla.*—Shape: Bilabiate. Aspect: Facing outward. Length: Approximately 2.8 cm. Width: Approximately 2.4 cm. Depth: Approximately 1.1 cm.

*Petals.*—Quantity: 5 petals fused at base forming a throat and consisting of an upper lip with 2 petals and a lower lip with 3 petals, consisting of 2 lateral petals and one central petal. Shape: Obovate. Margin: Entire. Apex: Obtuse.

*Upper lip.*—Length of petals from throat: Approximately 8.0 mm. Width of each petal: Approximately 1.1 cm. Texture of upper surface: Sparsely glandular pubescent. Gland color: 154D, transparent. Texture of lower surface: Glabrous. Color of upper surface when fully open: Between N57A and N57B. Color of lower surface when fully open: N57C.

*Lower lip, lateral petals.*—Length of petals from throat: Approximately 1.0 cm. Width of each petal: Approximately 1.4 cm. Texture of upper surface: Sparsely glandular pubescent. Gland color: 154D, transparent. Texture of lower surface: Sparsely glandular pubescent. Gland color: Colorless, transparent. Color of upper surface when fully open: Between N57A and N57B with spots of 83A. Color of lower surface when fully open: N57C.

*Lower lip, central petal.*—Length from the palate: Approximately 9.0 mm. Width: Approximately 1.2 cm. Texture of upper surface: Sparsely glandular pubescent. Gland color: 154D, transparent. Texture of lower surface: Sparsely glandular pubescent. Gland color: Colorless, transparent. Color of upper surface when fully open: Between N57A and N57B with spots of 83A. Color of lower surface when fully open: N57C.

*Throat.*—Length: Approximately 1.0 cm. Width: Approximately: 7.0 mm. Texture of inner surface: Sparsely glandular pubescent. Gland color: Mixture of colorless and 154D, transparent. Texture of outer surface: Glabrous. Color of inner surface: NN155A tinted with 77B and 145B, spots and streaks of N186A. Color of outer surface: 146D with spots and streaks of N79A. Palate color: NN155A tinted with 77B, spots and streaks of N186A. Palate texture: Glabrous. Teeth color: 145C.

*Calyx.*—Shape: Star, cupped. Diameter: Approximately 6.0 mm.

*Sepals.*—Quantity per flower: 5, fused at base. Shape: Ovate. Apex: Acute. Length: Approximately 4.0 mm. Width: Approximately 2.0 mm. Texture of upper (inner) surface: Sparsely glandular pubescent. Gland color: Colorless, transparent. Texture of lower (outer) surface: Glabrous. Color of upper (inner) surface: N137A. Color of lower (outer) surface: N137A with a heavy overlay of N186A.

*Pedicel.*—Strength: Strong. Aspect: Acute angle to stem. Length: Approximately 2.5 cm. Diameter: Approximately 1.0 mm. Texture: Glabrous. Color: 144A with a heavy overlay of 187A.

*Reproductive organs.*—Androecium: Stamen quantity: 4 per flower. Filament length: Approximately 5.0 mm. Filament texture: Sparsely glandular pubescent. Gland color: Colorless, transparent. Filament color: NN155D tinted with N57D, opaque. Anther shape: Bilobed. Anther length: Approximately 1.0 mm. Anther color: N57D with 83A where anther opens. Pollen amount: Abundant. Pollen color: 155D. Gynoecium: Pistil quantity: 1 per flower. Pistil length: Approximately 5.0 mm. Stigma shape: Pointed. Stigma length: Less than 1.0 mm. Stigma color: NN155D, opaque. Style length: Approximately 3.0 mm. Style color: NN155D tinted with N57D near stigma, opaque. Ovary diameter: Approximately 2.0 mm. Ovary texture: Glabrous. Ovary color: 145A.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Balarcher', substantially as herein illustrated and described.

* * * * *